(12) United States Patent
Chiou

(10) Patent No.: US 12,377,031 B2
(45) Date of Patent: Aug. 5, 2025

(54) COSMETIC COMPOSITIONS COMPRISING 4-HYDROXYACETOPHENONE

(71) Applicant: L'OREAL, Paris (FR)

(72) Inventor: Catherine Chiou, Saddle Brook, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 17/038,928

(22) Filed: Sep. 30, 2020

(65) Prior Publication Data
US 2022/0096344 A1 Mar. 31, 2022

(51) Int. Cl.
| | |
|---|---|
| *A61K 8/34* | (2006.01) |
| *A61K 8/02* | (2006.01) |
| *A61K 8/06* | (2006.01) |
| *A61K 8/31* | (2006.01) |
| *A61K 8/35* | (2006.01) |
| *A61K 8/37* | (2006.01) |
| *A61K 8/39* | (2006.01) |
| *A61K 8/42* | (2006.01) |
| *A61K 8/67* | (2006.01) |
| *A61K 8/81* | (2006.01) |
| *A61Q 1/14* | (2006.01) |
| *A61Q 19/00* | (2006.01) |
| *A61Q 19/10* | (2006.01) |

(52) U.S. Cl.
CPC ............ *A61K 8/347* (2013.01); *A61K 8/0208* (2013.01); *A61K 8/062* (2013.01); *A61K 8/064* (2013.01); *A61K 8/066* (2013.01); *A61K 8/31* (2013.01); *A61K 8/35* (2013.01); *A61K 8/37* (2013.01); *A61K 8/375* (2013.01); *A61K 8/39* (2013.01); *A61K 8/42* (2013.01); *A61K 8/675* (2013.01); *A61K 8/8152* (2013.01); *A61Q 1/14* (2013.01); *A61Q 19/00* (2013.01); *A61Q 19/10* (2013.01); *A61K 2800/48* (2013.01); *A61K 2800/524* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 9,107,853 B2 | 8/2015 | Pan et al. | |
| 2004/0081679 A1* | 4/2004 | Simon | A61Q 1/14 424/443 |
| 2004/0219115 A1* | 11/2004 | Kini | A61K 8/675 424/62 |
| 2010/0227011 A1* | 9/2010 | Kuhlman | A61Q 19/02 424/60 |
| 2010/0303746 A1* | 12/2010 | Mongiat | A61K 8/494 424/59 |
| 2018/0243189 A1* | 8/2018 | Pruns | A61K 8/361 |
| 2019/0021961 A1* | 1/2019 | Abels | A61P 17/16 |
| 2019/0290575 A1* | 9/2019 | Norman | A61K 8/602 |
| 2020/0039911 A1 | 2/2020 | Pillai et al. | |
| 2020/0179404 A1* | 6/2020 | Bode | A61K 31/573 |

FOREIGN PATENT DOCUMENTS

| | | | |
|---|---|---|---|
| CN | 107 260 582 A | 10/2017 | |
| CN | 110 292 557 A | 10/2019 | |
| EP | 2774481 A1 | 9/2014 | |
| KR | 101991248 B1 * | 6/2019 | ............... A61K 8/89 |
| WO | 2015144326 A1 | 10/2015 | |
| WO | 2017172519 A1 | 10/2017 | |
| WO | WO-2019086327 A1 * | 5/2019 | ........... A61K 31/455 |

OTHER PUBLICATIONS

"Isohexadecane", CosmetoScope (Feb. 9, 2017) (an internet article obtained from the website http://cosmetoscope.com/2017/02/isohexadecane/) (Year: 2017).*
MacLeman "PEG-7 Glyceryl Cocoate: Is It Safe?", The DERM Review (Jun. 11, 2020) (an internet article obtained from the website : https://thedermreview.com/peg-7-glyceryl-cocoate/) (Year: 2020).*
"Isopropyl What? Why You Need to Know About This Ingredient", Vaunt (Sep. 18, 2017) (an internet article obtained from the website: https://botaneri.com/skincare-ingredients-isopropyl-myristate/) (Year: 2017).*
"Carbomer", The Skincare Chemist (Jul. 9, 2009) (an internet article obtained from the website: https://www.theskincarechemist.com/glossary/carbomer/) (Year: 2009).*
Shechter "Pharmaceutical Creams: Water or Oil Emulsion?", Bee International (Sep. 30, 2015) (an internet article obtained from https://www.beei.com/blog/pharmaceutical-creams-water-or-oil-emulsion) (Year: 2015).*
"NIRS for the Determination of Water Content in Moisturizing Skin Creams", News Medical Life Sciences (Mar. 1, 2019) (an internet article obtained from the website: https://www.news-medical.net/whitepaper/20190301/NIRS-for-the-Determination-of-Water-Content-in-Moisturizing-Skin-Creams.aspx) (Year: 2019).*
Taylor ("Isopropyl Myristate", a product sheet obtained from the website https://file.wuxuwang.com/hpe/HPE6/HPE6_152.pdf (Jan. 28, 2009)) (Year: 2009).*
Essaidi et al ("Phytochemical investigation of *Tunisian Salicornia herbacea* L., antioxidant, antimicrobial and cytochrome P450 (CYPs) inhibitory activities of its methanol extract", Food Control, vol. 32 (2013), p. 125-133).*
English translation of KR-101991248-B1 (2019).*
Search Report issued to counterpart French Application No. 2013088 dated Sep. 22, 2021.

(Continued)

*Primary Examiner* — Sin J Lee
(74) *Attorney, Agent, or Firm* — McNees Wallace & Nurick LLC

(57) ABSTRACT

A cosmetic composition including a water phase, the water phase comprising solubilized 4-hydroxyacetophenone with niacinamide, wherein the weight ratio of niacinamide to 4-hydroxyacetophenone in the water phase is greater than 3.0.

19 Claims, No Drawings

(56) References Cited

OTHER PUBLICATIONS

Anonymous, Mintel "Ultra-Smoothing Anti-Ageing Lifting Eye Cream" XP055843467, No. 7146493, Jan. 3, 2020, www.gnpd.com.
Anonymous, Mintel "Deep Sea Make-Up Removing Mousse" XP055843507, No. 7572399, Apr. 24, 2020, www.gnpd.com.
Anonymous, Mintel "Niacinamide Stablizing Brightening Cream" XP055843509, No. 7268933, Feb. 17, 2020, www.gnpd.com.
Koparkar et al. "Solubility of o-/p- Hydroxyacetophenones in Aqueous Solutions of Sodium Alkyl Benzene Sulfonate Hydrotropes", Journal of Chemical and Engineering Data, vol. 49, No. 4, Jul. 1, 2004, pp. 800-803.
Choudhary "Solubility Enhancement of Escitalopram Oxalate Using Hydrotrop", International Journal of Pharmacy and Pharmaceutical Sciences, vol. 5, No. 1, Jan. 1, 2013, pp. 121-125, http://www.ijppsjournal.com/vol5Issue1/6105.pdf.
Oliveira-Alves et al. "Impact of Drying Processes on the Nutritional Composition, Volatile Profile, Phytochemical Content and Bioactivity of Salicornia ramosissima J. Woods," Antioxidants, 2021, 10, 1312.
Rahmani et al. "Correction: biochemical composition and biological activities of *Salicornia europaea* L. from southern Tunisia," Journal of Food Measurement and Characterization, Sep. 2022, ResearchGate.

\* cited by examiner

COSMETIC COMPOSITIONS COMPRISING 4-HYDROXYACETOPHENONE

FIELD OF THE INVENTION

This invention relates to cosmetic compositions including a water phase having solubilized 4-hydroxyacetophenone.

BACKGROUND OF THE INVENTION

Chemical preserving agents are known to be incorporated into cosmetic or dermatological compositions. These preserving agents are intended to combat the growth of microorganisms in these compositions, which would quickly make them unsuitable for use. It is in particular necessary to protect compositions against microorganisms capable of growing inside the composition, for example during production thereof, and also against those which the user might introduce therein while handling it, in particular when taking up products in jars with the fingers.

One suitable chemical preserving agent that has been incorporated into certain cosmetic products is 4-hydroxyacetophenone. However, 4-hydroxyacetophenone has limited solubility in water and typically requires heating to temperatures at or greater than 60° C. in order to solubilize the 4-hydroxyacetophenone into aqueous systems. Heating to provide the solubilization of 4-hydroxyacetophenone is an energy-consuming and costly process. In addition, certain ingredients and materials associated with cosmetic or dermatological compositions are adversely affected by exposure to such increased temperatures. Accordingly, there is a need for cosmetic compositions having a stable water phase including 4-hydroxyacetophenone that have not been exposed to increased temperatures.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In accordance with various embodiments, provided is a cosmetic composition including a water phase having solubilized 4-hydroxyacetophenone with niacinamide is formed by the steps consisting essentially of providing an aqueous composition and combining 4-hydroxyacetophenone and niacinamide.

In one embodiment, the water phase includes 4-hydroxyacetophenone in an amount from about 0.2% to about 1.0%, by weight, based on the weight of the water phase and niacinamide in an amount from about 1% to about 5%, by weight, based on the weight of the water phase. The weight ratio of niacinamide to 4-hydroxyacetophenone in the water phase is greater than 3.0.

In another embodiment, the cosmetic composition is formed by providing the water phase having the solubilized 4-hydroxyacetophenone with niacinamide and adding components selected from the group consisting of water, humectants, preservatives, emollients, surfactants, emulsifiers, active compounds and combinations thereof.

In another embodiment, provided is a cosmetic composition including a water phase, the water phase comprising solubilized 4-hydroxyacetophenone with niacinamide, wherein the weight ratio of niacinamide to 4-hydroxyacetophenone in the water phase is greater than 3.0.

In another embodiment, provided is a makeup removal and cleansing article, having a water-insoluble substrate impregnated in the water-insoluble substrate a solubilized 4-hydroxyacetophenone with niacinamide.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

DETAILED DESCRIPTION OF THE INVENTION

The term "article" is understood here to mean the combination composed of a water-insoluble support and a composition impregnated on the support. This article can in particular be a wipe but it can also have any form including those described below. The water-insoluble substrate is absorbent and sufficiently strong not to disintegrate during the use thereof. The use of the article as defined above for caring for the skin or hair and/or cleaning and/or removing makeup from and/or scrubbing the skin.

"Keratinous substrate" and "keratinous tissue" each includes but is not limited to skin, hair, and nails.

"Cosmetically acceptable" means a carrier that is compatible with any keratinous substrate.

The solubilized 4-hydroxyacetophenone forms a water phase for use in a cosmetic composition. The cosmetic composition may be any suitable cosmetic composition such as skin care products, such as, but not limited to, make-up remover, cleanser, micellar water, water-in-oil or oil-in-water emulsion, multi-phase compositions comprising at least one water phase.

In another embodiment, the cosmetic composition is formed by providing the water phase having the solubilized 4-hydroxyacetophenone with niacinamide and adding components selected from the group consisting of water, humectants, preservatives, emollients, surfactants, emulsifiers, active compounds and combinations thereof.

The cosmetic composition having the water phase including solubilized 4-hydroxyacetophenone with niacinamide is formed by the steps consisting essentially of providing an aqueous composition and combining 4-hydroxyacetophenone and niacinamide. In one embodiment, the water phase includes 4-hydroxyacetophenone in an amount from about 0.2% to about 1.0%, by weight, based on the weight of the water phase and niacinamide in an amount from about 1% to about 5%, by weight, based on the weight of the water phase. The weight ratio of niacinamide to 4-hydroxyacetophenone in the water phase is greater than 3.0.

4-Hydroxyacetophenone

The composition, according to the present invention, includes 4-hydroxyacetophenone. As utilized herein, "4-hydroxyacetophenone" includes 4-hydroxyacetophenone and derivatives thereof.

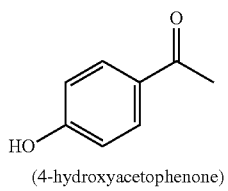

(4-hydroxyacetophenone)

By derivatives of 4-hydroxyacetophenone, it is meant that 4-hydroxyacetophenone includes cosmetically acceptable salts of derivatives. In particular, the sodium and potassium and ammonium salts of compounds of 4-hydroxyacetophenone. In some cases, the utilization of the respective ionic compound or solvate carrier proves to be superior to the unmodified derivative.

The 4-hydroxyacetophenone present in the water phase of the cosmetic composition according to the present invention is present in an amount of at least 0.02% by weight, or at least about 0.05% by weight, or at least about 0.1% by weight, or at least about 0.15% by weight, or at least about 0.20% by weight, or at least about 0.25% by weight, or at least about 0.30% by weight, or at least about 0.35% by weight, or from about 0.02% to about 1.0%, or from about 0.1% to about 0.9%, or from about 0.2% to about 0.8%, or from about 0.3% to about 0.7%, or from about 0.4% to about 0.6%, about 0.5% or any suitable combination, sub-combination, range, or sub-range thereof by weight, based on the weight of the cosmetic composition. One of ordinary skill in the art, however, will appreciate that other ranges are within the scope of the invention.

Thus, 4-hydroxyacetophenone is present in an amount by weight, based on the total weight of the cosmetic composition, from about 0.02, 0.03, 0.04, 0.05, 0.06, 0.07, 0.08, 0.09, 0.10, 0.20, 0.30, 0.40, 0.50, 0.60, 0.70, 0.80, or 0.90, to about 1.0 weight percent, including increments and ranges therein and there between.

Niacinamide

The composition, according to the present invention, includes niacinamide. As utilized herein, "niacinamide" includes niacinamide and derivatives thereof. Niacinamide is Vitamin B3 or PP (niacinamide) the derivatives of these vitamins (in particular esters) and their mixtures. This material is alternatively known as nicotinic acid amide and vitamin B3. Suitable niacinamide compounds or derivatives thereof are chosen from known nicotinic acid (or niacin), nicotinamide riboside, niacinamide ascorbate, and salts of thereof, and/or a combination thereof.

The niacinamide present in the water phase of the cosmetic composition according to the present invention is present in an amount of at least 1.0% by weight, or at least about 1.2% by weight, or at least about 1.4% by weight, or at least about 1.6% by weight, or at least about 1.8% by weight, or at least about 2.0% by weight, or at least about 2.2% by weight, or at least about 2.5% by weight, or from about 1.0% to about 5.0%, or from about 1.5% to about 4.5%, or from about 2.0% to 4.0%, or from about 2.5% to about 3.5%, or about 1.5% or about 2.0% or about 3.0%, or any suitable combination, sub-combination, range, or sub-range thereof by weight, based on the weight of the cleansing composition. One of ordinary skill in the art, however, will appreciate that other ranges are within the scope of the invention.

Thus, niacinamide is present in an amount by weight, based on the total weight of the cosmetic composition, from about 1.0, 1.2, 1.4, 1.6, 1.8, 2.0, 2.2, 2.4. 2.6, 2.8, 3.0, 3.2, 3.4, 3.6, 3.8, 4.0, 4.2, 4.4, 4.6, or 4.8, to about 5.0 weight percent, including increments and ranges therein and there between.

In one embodiment, the niacinamide is present in a weight ratio with respect to 4-hydroxyacetophenone greater than 3.0. Thus, the ratio of niacinamide, on a weight basis, at least 3.0, or at least about 3.2, or at least about 3.4, or at least about 3.6, or at least about 3.8, or at least about 4.0, or at least about 4.2, or at least about 4.6, or at least about 4.8, or at least about 5.0, or from about 3.0 to about 5.0, or from about 3.0 to about 4.0, or from about 3.2 to about 3.8, or from about 3.4 to about 3.6 or about 3.0 or about 3.5 or about 4.0, or any suitable combination, sub-combination, range, or sub-range thereof by weight, based on the weight of the cosmetic composition.

In one embodiment of the present invention, the niacinamide and 4-hydroxyacetophenone are combined to form a solubilized 4-hydroxyacetophenone. By solubilized 4-hydroxyacetophenone, as utilized herein, it is meant that the composition including 4-hydroxyacetophenone is a stable composition where the 4-hydroxyacetophenone has been solvated such that no or a minimal amount of solid is present in the composition. The stability of the composition is such that exposure to storage at low temperatures, such as temperatures of 4° C. in a controlled chamber for one week, results in little or no visible precipitation of solid 4-hydroxyacetophenone in the solution.

In one embodiment, a cosmetic composition is formed. The cosmetic composition is formed by providing the water phase having the solubilized 4-hydroxyacetophenone with niacinamide. Components are added to the water phase solubilized 4-hydroxyacetophenone with niacinamide and are mixed to form the cosmetic composition. Suitable components that may be added may be selected from the group consisting of water, humectants, preservatives, emollients, surfactants, emulsifiers, active compounds and combinations thereof.

In addition to cosmetic compositions, embodiments of the present invention include articles utilizing the cosmetic compositions according to the present invention. In some embodiments, the article may be formed of synthetic materials, such as PET (Polyethylene terephthalate, or polyester) and PP (polypropylene), which may be used alone or in combination with natural-based material. And in some embodiments, the article may be formed of sustainable and biodegradable substrates from sources, such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton.

Many conventional cosmetic articles, such as wipes, are formed of fossil-based polymeric materials, such as PET (Polyethylene terephthalate, or polyester) and PP (polypropylene), which may be used alone or in combination with natural-based material. Such synthetic substrates are desirable because they are relatively less costly to produce and deliver good tensile strength, however, because they essentially never degrade, they contribute adversely to the environment. With increasing focus in the cosmetics industry on sustainability, there is a need for cosmetic articles that employ solid substrates to draw from sources, such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton. As used herein, the terms "natural originated fiber" refers to fiber materials that are formed by chemical processing that render derivatives based on natural fibers; "natural fiber" means non-derivative forms of natural fibers, and "regenerated/recycled" means natural fibers that are reclaimed from goods formed with such fibers.

In some embodiments, the article herein is formed of substrates that are obtained from sustainable sources and are biodegradable. In some particular embodiments, these materials are selected from natural originated fiber formed into nonwovens, using fibers, such as pulp, viscose, lyocell, cellulose acetate, and cotton. And in certain embodiments, the substrates used to form cosmetic articles are nonwovens of lyocell. According to those embodiments that include natural biodegradable and sustainably sourced fibers, a clear benefit realized is the opportunity to reduce the environmental burden. Other benefits may also be achieved using sustainable and biodegradable substrates. As further described herein, exemplified articles that employ sustainable and biodegradable substrates, particularly lyocell nonwovens, demonstrate unexpected mechanical, textural, and absorbent properties and significantly enhanced performance as compared with competitive cosmetic articles that employ synthetic materials. Also as described herein, exemplified articles that employ sustainable and biodegradable substrates, particularly lyocell nonwovens, demonstrate enhanced performance even as compared with inventive compositions hereof that are imbued in a synthetic substrate.

An article according to the disclosure is moist to the touch. It exhibits the advantage of being comfortable during application to the skin and having a nourishing effect due to the presence of an oily phase. When it is used for cleaning or removing makeup from the skin, an article according to the disclosure is passed over the skin, while possibly leaving it applied for a time sufficient for the makeup products to be dissolved in the impregnating composition of the article, and then the skin is wiped. The skin can also optionally be rinsed subsequently. The article according to the invention is preferably a cosmetic article appropriate for caring for and/or treating the skin of the face, body or hands and for cleaning or removing makeup from the skin of the face and/or body. It can also be used for caring for the hair and for removing makeup from the eyes.

An article according to the disclosure can have any form appropriate to the desired objective. It can constitute a wipe that has a generally rectangular, square or other shape that may be single ply, multiple ply, and may be folded or un-folded. The article can also be in the form of a glove, of a mitten or in any other form appropriate for practical use on the face or the body, for example, in the form of a face with holes for the sites of the eyes, nose and/or mouth, or in the form of a makeup-removing fingerstall for application in removing makeup from the eyelashes, or in the form of a single- or double-sided disc which can in particular comprise two sides impregnated with different compositions. The article can also comprise a rough surface which makes possible the exfoliation (scrubbing) of the skin.

According to the disclosure, the inventive compositions overcome the shortcomings of the prior art and provide unexpected benefits that include ease with overall makeup removal, easy foundation removal, leaves skin feeling clean and fresh, soft and smooth, easy mascara removal (regular and waterproof) with no rubbing, satisfying size and thickness of substrate (wipe), not too dry, non-greasy, does not leave a residue and pleasant fragrance.

Through expert evaluations of makeup removal efficacy, compositions according to the disclosure demonstrated significantly better performance in removing waterproof mascara and long-wear foundation as compared with currently marketed makeup removal wipes, for example, Neutrogena™ Makeup Remover Cleansing Towelettes and Garnier™ SkinActive Clean+ Refreshing Remover Cleansing Towelettes, both formed with synthetic fiber substrates imbued with cleansing compositions.

In a consumer study, inventive compositions according to the disclosure not only performed better in makeup removal efficacy, including improved performance in the removal of both foundation and mascara, but also provided an experience for consumer testers that was more pleasing and resulted in comparatively better skin feel after use. Inventive articles formed using natural fiber demonstrated similar enhanced performance versus comparative compositions and also versus the same inventive compositions imbued in synthetic fiber substrate. The compositions according to the disclosure have a clean and fresh feel when applied, and do not leave skin feeling greasy or sticky.

Compositions according to the disclosure include at least one branched or linear, liquid alkane with carbon chain length of C11 to C20, at least one polar emollient with molecular weight of 400 g/mol or less, at least one polymeric thickener for water-based system, and at least one alkylated glycerol ester in a water-based emulsion/suspension system comprising oily and water phases, the water phase including water present from about 70% to about 85% by weight of the composition. In various embodiments, the compositions may include more than one of each of the components, and may further include one or more additives including humectants, preservatives, fragrances, actives, and pH adjusters, among other cosmetically acceptable additives.

(I) Branched or Linear, Liquid Alkane

In accordance with the disclosure, the compositions include at least one branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes. In some exemplary embodiments, such liquid alkanes may be chosen from isoparaffins, for instance, isododecane (also known as 2,2,4,4,6-pentamethylheptane), isodecane, and isohexadecane.

In some embodiments, the at least one branched or linear, liquid alkane comprises isohexadecane, C15-19 alkane, isododecane, undecane, tridecane and combinations thereof. In some embodiments the composition comprises two or more branched or linear, liquid alkanes. In some such embodiments, the branched or linear, liquid alkane comprises isohexadecane.

The amount of each of the at least one branched or linear, liquid alkane is present in the composition in a range of from about 1% to about 12% by weight, or from about 3% to about 11% by weight, or from about 5% to about 10% or any suitable combination, sub-combination, range, or sub-range thereof by weight, based on the weight of the composition. One of ordinary skill in the art, however, will appreciate that other ranges are within the scope of the invention.

Thus, each of the at least one branched or linear, liquid alkane in the composition may be present by weight, based on the total weight of the composition, from about 1, 2, 3, 4, 5, 6, 7, 8, 9, to about 10 percent, including increments and ranges therein and there between.

(ii) Polar Emollients

In accordance with the disclosure, the compositions include at least one polar emollient. Emollients are oil-phase ingredients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol to about 350 g/mol.

In some embodiments, suitable polar emollients that may be used according to the disclosure include those derived from C12-050 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/ caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

In some embodiments, the one or more polar emollient comprises one of isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, and combinations thereof. In some particular embodiments the one or more polar emollient includes isopropyl myristate. In some embodiments the composition comprises two or more polar emollients. In some such embodiments, the polar emollient comprises isopropyl myristate and one or more additional polar emollients.

The amount of each of the at least one polar emollient is present in the composition in a range of from about 1% to about 12% by weight, or from about 3% to about 11% by weight, or from about 5% to about 10% or any suitable combination, sub-combination, range, or sub-range thereof by weight, based on the weight of the composition. One of ordinary skill in the art, however, will appreciate that other ranges are within the scope of the invention.

Thus, each of the at least one polar emollient in the composition may be present by weight, based on the total weight of the composition, from about 1, 2, 3, 4, 5, 6, 7, 8, 9, to about 10 percent, including increments and ranges therein and there between.

(iii) Polymeric Thickener

In accordance with the various embodiments, the compositions include one or more polymeric thickeners. In some embodiments, the one or more thickener may be selected from one or more of natural gums and synthetic polymers, for example, starches (corn, rice, tapioca, potato), gums (xanthan carrageenan, gellan, *sclerotium*, tarabiotech fermentation). In some particular embodiments, the thickener may be selected from acrylates/C10-30 alkyl acrylate crosspolymer, carbomer, xanthan gum, hydroxypropyl guar, *Ceratonia siliqua* (carob) gum, ammonium polyacryloyldimethyl taurate, ammonium acryloyldimethyltaurate/ steareth-25 methacrylate crosspolymer, and polyacrylate crosspolymer-6.

In some embodiments, the polymeric thickener is one of carbomer, acrylates/C10-30 alkyl acrylate crosspolymer, polyacrylate crosspolymer-6, microcrystalline cellulose (and) cellulose gum, xanthan gum, sodium carboxymethyl starch, *sclerotium* gum (and) xanthan gum, xanthan gum (and) *Ceratonia siliqua* (carob) gum (50/50), dehydroxanthan gum, hydroxypropyl starch phosphate, *sclerotium* gum (and) xanthan gum (75/25), *sclerotium* gum, xanthan gum (and) *sclerotium* gum (and) Lecithin (and) pullulan, and combinations thereof.

In some embodiments the composition comprises two or more polymeric thickeners. In some such embodiments, the polymeric thickener comprises one or both of acrylates/C10-30 alkyl acrylate crosspolymer and carbomer, and optionally one or more additional polymeric thickeners.

The amount of each of the at least one polymeric thickener is present in the composition in a range of from about 0.01% to about 2%, or from about 0.01% to about 1.5%, or from about 0.3% to about 1.2%, or any suitable combination, sub-combination, range, or sub-range thereof by weight, based on the weight of the composition. One of ordinary skill in the art, however, will appreciate that other ranges are within the scope of the invention.

In some embodiments, the total amount of polymeric thickener in the composition is present from about 0.01% to about 5%, or from about 0.02% to about 2%, or from about 0.03% to about 1.5%, or from about 0.1% to about 0.2%, or any suitable combination, sub-combination, range, or sub-range thereof by weight, based on the weight of the composition. One of ordinary skill in the art, however, will appreciate that other ranges are within the scope of the invention.

Thus, one or more polymeric thickener is present by weight, based on the total weight of the composition, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

(iv) Alkylated Glycerol Ester/Surfactant

In accordance with the various embodiments, the compositions include at least one alkylated glycerol ester/surfactant. In some embodiments, the one or more surfactant may be selected from esters of polyols with fatty acids with a saturated or unsaturated chain containing, for example, from 8 to 24 carbon atoms (e.g., 12 to 22 carbon atoms), and alkoxylated derivatives thereof, such as glyceryl esters of a C8-C24 fatty acid or acids and alkoxylated derivatives thereof, polyethylene glycol esters of a C8-C24 fatty acid or acids and alkoxylated derivatives thereof, sorbitol esters of a C8-C24 fatty acid or acids and alkoxylated derivatives thereof, sugar (sucrose, glucose, alkylglycose) esters of a C8-C24 fatty acid or acids and alkoxylated derivatives thereof, ethers of fatty alcohols, ethers of sugar and a C8-C24 fatty alcohol or alcohols, and mixtures thereof.

In some embodiments the composition comprises at least one, and in some embodiments, two or more alkylated glycerol esters. In some such embodiments, the alkylated glycerol ester comprises one or more of PEG-7 glyceryl cocoate, PEG-7 caprylic/capric glycerides, PEG-6 caprylic/ capric glycerides, disodium cocoyl glutamate (and) sodium cocoyl glutamate, coco-Betaine, caprylyl/capryl glucoside, Disodium cocoamphodiacetate, sodium cocoamphoacetate, polyglyceryl-4 caprate, and combinations thereof.

In some embodiments, each of the at least one alkylated glycerol ester in the composition is present from about 0.1% to about 2%, or from about 0.2% to about 1.5%, or from about 0.5% to about 1%, or any suitable combination, sub-combination, range, or sub-range thereof by weight, based on the weight of the composition. One of ordinary skill in the art, however, will appreciate that other ranges are within the scope of the invention.

In some particular embodiments, the total amount of alkylated glycerol ester/surfactant is present up to about 2%. In some embodiments the total amount of alkylated glycerol ester/surfactant does not exceed about 2%. In some particular embodiments, the total amount of alkylated glycerol ester/surfactant is less than about 2%.

Thus, each of the at least one alkylated glycerol ester is present by weight, based on the total weight of the composition, from about 0.1, 0.2, 0.3, 0.4, 0.5, 0.55, 0.6, 0.7, 0.75, 0.8, 0.9, 1.0, 1.1, 1.2, 1.3, 1.4, 1.5, 1.6, 1.7, 1.8, 1.9, to about 2.0 percent, including increments and ranges therein and there between.

(v) Solvent/Water

In accordance with the various embodiments, water is present in the compositions in a range from about 60% to about 90%, or from about 65% to about 85%, or from about 70% to about 85%, or from about 75% to about 80%, or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 60, 65, 70, 75, 80, 85, to about 90 weight percent, including increments and ranges therein and there between.

The water used may be sterile demineralized water and/or a floral water, such as, rose water, cornflower water, chamomile water or lime water, and/or a natural thermal or mineral water, such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements, such as, zinc, copper, magnesium, etc., reconstituting the characteristics of a thermal water.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example, ammonia or a primary, secondary or tertiary (poly)amine, such as, monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the composition can include one or more additional solvents, for example, monoalcohols, such as monohydric C1-C8, alcohols, such as, ethanol, propanol, butanol, isopropanol, isobutanol, and benzyl alcohol, and phenylethyl alcohol.

Humectant/Hydrating Agent

In accordance with the disclosure, one or more humectants may be present in the compositions. In some embodiments, the humectant may comprise one or more of polyols, including, for example, glycerin, glycerol, glycols, such as, caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers, such as, monopropylene, dipropylene and tripropylene glycol alkyl($C_1$-$C_4$)ethers, squalane, triacetin, sugars, such as, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the compositions include a humectant comprising glycerin.

In accordance with the various embodiments, the amount of humectant present in the compositions can range from about 1% to about 10%, or from about 1% to about 8%, or from about 1% to about 5%, or from about 2% to about 3%, or any suitable combination, sub-combination, range, or sub-range thereof by weight, based on the weight of the composition. One of ordinary skill in the art, however, will appreciate that other ranges are within the scope of the invention.

Thus, any one of or a combination of humectant may be present, by weight, based on the total weight of the composition, is from about 1, 2, 3, 4, 5, 6, 7, 8, 9, to about 10 weight percent, including increments and ranges therein and there between.

Optional Additives

The compositions can also comprise at least one additive used in the cosmetics field which does not affect the properties of the compositions according to the invention, such as, fragrances, pearlescent agents, silica, preservatives, proteins, protein hydrolysates, vitamins, panthenol, silicones, odor absorbers and coloring materials; anti-microbial components, including, but not limited to, capryloyl glycine and sodium salicylate; essential oils; fruit extracts, for example, *Pyrus* Malus (Apple) Fruit Extract, and Aloe Barbadensis Leaf Juice Powder; citric acid, sodium chloride; neutralizing or pH-adjusting agents (e.g., triethylamine (TEA) and sodium hydroxide), preservatives, and combinations thereof. In some embodiments, the compositions include at least one preservative comprising one or a combination of hydroxyacetophenone and caprylyl glycol.

Although the optional active additives are given as examples, it will be appreciated that other optional components compatible with cosmetic applications known in the art may be used. Although the optional additives are given as examples, it will be appreciated that other optional components compatible with cosmetic applications known in the art may be used.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Substrate

In accordance with the various embodiments, provided are articles comprising a solid substrate imbued with an inventive cosmetic composition. The makeup removal and cleansing article is formed from synthetic materials or formed from natural biodegradable and sustainably sourced natural originated fiber, natural fiber, or regenerated or recycled natural fiber.

According to some embodiments, the substrate is a nonwoven material. A general description of nonwoven materials is given in Riedel "Nonwoven Bonding Methods and Materials", Nonwoven World (1987). These substrates are obtained according to the normal methods of the technology for the preparation of nonwoven materials.

When the substrate is a nonwoven material, use may be made of a nonwoven material which does not go into ball and which is sturdy enough not to disintegrate and not to become fluffy when applied to the skin. It must be absorbent and soft at least on one side for the removal of makeup from the eyes in particular. Mention may be made, as appropriate nonwoven materials, for example, of those sold under the names Ultraloft 15285-01, Ultraloft 182-008, Ultraloft 182-010 and Ultraloft 182-016 by BBA, Vilmed M1519 Blau, Vilmed M 1550 N and 112-132-3 by Freudenberg, that sold under the name Norafin 11601-010B by Jacob Holm Industries, the flocked nonwoven materials sold under the names Univel 109 and Univel 119 by Uni Flockage and that made of viscose/PLA supplied by Sandler.

According to some embodiments comprising an article, a water insoluble substrate is employed. The water-insoluble substrate can comprise one or more layers and it can be chosen from the group consisting of woven materials, nonwoven materials, foams, sponges, waddings, as sheets, balls or films. It can, in particular, be a nonwoven substrate based on fibers of natural origin (flax, wool, cotton, silk, viscose, fibers made of bamboo) or synthetic origin (cellulose derivatives, polyvinyl derivatives, polyesters, such as poly(ethylene terephthalate), polyolefins, such as polyethylene (PET) or polypropylene, polyamides, such as Nylon, or acrylic derivatives) and their mixtures, such as viscose/PET, polylactic acid (PLA) or viscose/polylactic acid (viscose/PLA).

According to one embodiment, the substrate is a nonwoven material, composed of viscose or a nonwoven material composed of a viscose/microviscose mixture, through a hydro entanglement process.

In some particular embodiments, the makeup removal and cleansing article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations thereof.

According to one embodiment, the substrate is a nonwoven material formed of a biodegradable material, such as lyocell.

According to some embodiments, the substrate can comprise one or more layers having identical or different properties and having properties of elasticity and of softness and other properties appropriate to the desired use. The substrates can comprise, for example, two parts having different elasticity properties, as described in the document WO-A-99/13861, or can comprise a single layer having different densities, as described in the document WO-A-99/25318, or can comprise two layers of different textures, as described in the document WO-A-98/18441.

According to some embodiments, when the article is used for the body, the substrate can comprise at least one rough side for making it possible, at the same time, to massage the skin or to scrub the skin.

According to the various embodiments, the substrate can have any size and any shape which are appropriate for the desired objective. Furthermore, it generally has a surface area of between 0.005 $m^2$ and 0.1 $m^2$, or from between 0.01 $m^2$ and 0.05 $m^2$. The weight of the substrate can be in a range between 30 gsm to 200 gsm (gram per square meter), or from between 40 gsm to 60 gsm.

According to the various embodiments, the degree of impregnation of the composition onto the substrate generally ranges from 100% to 1000%, in some embodiments from about 150% to about 700%, or from about 250% to about 400% of the weight of the substrate. The techniques for impregnating the substrates with compositions are well known and can all be applied in the present invention. Generally, the impregnating composition is heated and added to the substrate by one or more techniques comprising immersion, coating, spraying, and the like.

The examples below according to the invention are given by way of illustration and without a limiting nature. The names are the chemical name or the INCI name. The amounts are given therein as % by weight, unless otherwise mentioned.

EXAMPLES

Example 1: Raw Materials

TABLE 1

Raw Materials

| INCI Name | Source and Cosmetic Functions |
| --- | --- |
| 4-Hydroxyacetophenone 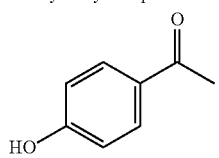 | SYMSAVE H ™; Symrise |
| Niacinamide 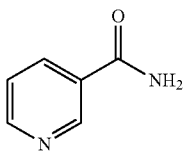 | Vitamin B3, co-solubilizer |
| Caffeine 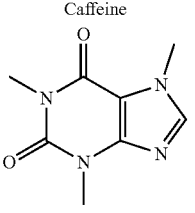 | Active compound, Co-solubilizer |

Example 2: Inventive and Comparative Compositions

TABLE 2

Inventive and Comparative Formulations

| Phase | INCI Name | Inventive Ex 1 Wt % | Comparative Ex 1 Wt % |
|---|---|---|---|
| A | WATER (QS) | 80.37 | 81.87 |
| A | GLYCERIN | 3 | 3 |
| A | NIACINAMIDE | 1.5 | |
| A | HYDROXYACETOPHENONE | 0.5 | 0.5 |
| A | HEXYLENE GLYCOL | 1 | 1 |
| A | TRISODIUM ETHYLENEDIAMINE DISUCCINATE | 0.1 | 0.1 |
| B | CARBOMER | 0.1 | 0.1 |
| B | ACRYLATES/C10-30 ALKYL ACRYLATE CROSSPOLYMER | 0.04 | 0.04 |
| C | Sodium Hydroxide | 0.04 | 0.04 |
| C | WATER | 1 | 1 |
| D | PIROCTONE OLAMINE | 0.05 | 0.05 |
| D | CAPRYLYL GLYCOL | 0.3 | 0.3 |
| D | ISOHEXADECANE | 5 | 5 |
| D | ISOPROPYL MYRISTATE | 5 | 5 |
| D | DICAPRYLYL ETHER | 1 | 1 |
| D | PEG-7 Glyceryl Cocoate | 1 | 1 |
| | Total (Wt %): | 100 | 100 |
| | Results: | White, smooth, fluid lotion, no visible solids | White fluid lotion with solids present |

Preparation of compositions of Table 2 processed at room temp (20-22° C.): 1. Prepare phase A by combining phase A ingredients and mixing well using a Reyneri mixer at 500-600 rpm for at least 20 min. until all ingredients are solubilized, giving a colorless, clear solution. If needed, use rotor stator (Silverson) to break down hydroxyacetophenone particulates. 2. Add phase B to phase A by slowly adding polymeric thickeners to water and mixing well until homogeneous and have no lumps or gel bodies. 3. Prepare pH adjuster by mixing sodium hydroxide in water (Phase C) and add to the AB. Mix well until smooth. 4. Add D (oil phase to ABC and mix until smooth). Take specifications (pH, viscosity).

TABLE 3

Solubility of Hydroxyacetophenone with Niacinamide

| Phase | INCI Name | INV EX 2 % | INV EX 3 % | COMP EX 2 % | COMP EX 3 % | COMP EX 4 % |
|---|---|---|---|---|---|---|
| A | WATER | QS | QS | QS | QS | QS |
| A | NIACINAMIDE | 2 | 1.5 | 1 | 0.5 | |
| B | HYDROXYACETOPHENONE | 0.5 | 0.5 | 0.5 | 0.5 | 0.5 |
| | N/H wt. ratio | 4 | 3 | 2 | 1 | 0 |
| | Results: | Fully dissolved, giving a colorless, clear solution (a few min) | Fully dissolved, giving a colorless, clear solution (20 min) | >95% solids dissolved, but some residual solids still visible after 40 min of mixing. Fully dissolved after prolonged mixing (>60 min). | Not dissolving, solids of hydroxyacetophenone present in the solution mixture | Not dissolved, solids of hydroxyacetophenone present in the solution mixture. |
| | Stored at 4° C. Chamber for 1 week | Remained as a colorless, clear solution, no crystals | Remained as a colorless, clear solution, no crystals | Crystals of hydroxyacetophenone present. | NA | NA |

Preparation of compositions of Table 3 processed at room temp (20-22° C.): 1. Prepare phase A by adding niacinamide (solids) to water and mix well until all solids dissolved (a few min.) using a Reyneri mixer at 500-600 rpm for at least 20 min. until all ingredients are solubilized, giving a colorless, clear solution. Thereafter, phase B hydroxyacetophenone (solids) is added to the phase A solution and is mixed well until all solids are dissolved.

TABLE 4

Solubility of Hydroxyacetophenone with Caffeine

| Phase | INCI Name | COMP EX 5 % | COMP EX 6 % | COMP EX 7 % |
|---|---|---|---|---|
| A | WATER | QS | QS | QS |
| A | CAFFEINE | 2 | 1 | 0.5 |
| B | HYDROXYACETOPHENONE | 0.5 | 0.5 | 0.5 |
| | Results: | Fully dissolved, giving a colorless, clear solution (10-15 min) | Fully dissolved, giving a colorless, clear solution (10-15 min) | Fully dissolved, giving a colorless, clear solution (15-20 min) |
| | Stored at 4° C. Chamber for 1 week | Solids crushed out | Solids crushed out | Solids crushed out |

Preparation of compositions of Table 4 processed at room temp (20-22° C.): 1. Prepare phase A by adding caffeine to water and mix well until all solids dissolved, giving a colorless, clear solution. Thereafter, phase B hydroxyacetophenone (solids) is added to the phase A solution and is mixed well until all solids are dissolved.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out

What I claim:

1. A cosmetic composition comprising a water phase having solubilized 4-hydroxyacetophenone with niacinamide and an oil phase, the cosmetic composition being formed by the steps consisting essentially of providing an oil composition comprising at least one branched or linear, liquid alkane with carbon chain length of C11 to C20 comprising isohexadecane, at least one polar emollient with molecular weight of 400 g/mol or less, and at least one alkylated glycerol ester surfactant comprising PEG-7 glyceryl cocoate and combining the oil composition with an aqueous composition having each of 4-hydroxyacetophenone and niacinamide to form the cosmetic composition, wherein:
the cosmetic composition is free of essential oils other than fruit extracts, aloe vera extract, and seaweed extract;
one or more humectants may be present in the cosmetic composition;
the at least one polar emollient with molecular weight of 400 g/mol or less comprises isopropyl myristate present in an amount from about 4% to about 12% by weight, based on the total weight of the cosmetic composition;
the total amount of the one or more humectants is 5.5% by weight or less, based on the total weight of the cosmetic composition;
the niacinamide is present in an amount of 1% to 3.5%, based on the total weight of the cosmetic composition; and
the isohexadecane is present in an amount from about 4% to about 12% by weight, based on the total weight of the cosmetic composition.

2. The cosmetic composition of claim 1, comprising:
the 4-hydroxyacetophenone in an amount from about 0.15% to about 1.0%, by weight, based on the total weight of the cosmetic composition, wherein the weight ratio of niacinamide to 4-hydroxyacetophenone in the water phase is at least 3.0.

3. The cosmetic composition of claim 1, wherein the cosmetic composition further includes components selected from the group consisting of the one or more humectants, preservatives, emollients other than the at least one polar emollient, surfactants other than the at least one alkylated glycerol ester surfactant, emulsifiers, active compounds, and combinations thereof.

4. The cosmetic composition of claim 1, wherein the cosmetic composition is a product selected from the group consisting of a make-up remover, a cleanser, a micellar water, a water-in-oil emulsion, an oil-in-water emulsion, and a multi-phase composition.

5. The cosmetic composition of claim 1, wherein the niacinamide comprises niacinamide or its derivative chosen from nicotinic acid, nicotinamide riboside, niacinamide ascorbate, salts thereof, or a combination thereof.

6. The cosmetic composition of claim 1, further comprising:
at least one polymeric thickener for water-based system, wherein water is present in the cosmetic composition in an amount from about 70% to about 85% by weight of the cosmetic composition.

7. The cosmetic composition according to claim 6, wherein:
the at least one polymeric thickener for water-based system comprises carbomer and acrylate/C10-30 alkyl acrylate crosspolymer.

8. The cosmetic composition according to claim 6, wherein:
a) each of the at least one branched or linear, liquid alkane with carbon chain length of C11 to C20 comprising isohexadecane is present from about 5% to about 10% by weight of the cosmetic composition;
b) each of the at least one polar emollient with molecular weight of 400 g/mol or less comprising isopropyl myristate is present from about 5% to about 10% by weight of the cosmetic composition;
c) each of the at least one polymeric thickener for water-based system is present from about 0.01% to about 2% by weight of the cosmetic composition; and
d) the at least one alkylated glycerol ester surfactant comprising PEG-7 glyceryl cocoate is present up to 2.2% by weight of the cosmetic composition.

9. A cosmetic composition including a water phase and an oil phase, the oil phase comprising at least one branched or linear, liquid alkane with carbon chain length of C11 to C20 comprising isohexadecane, and at least one alkylated glycerol ester surfactant comprising PEG-7 glyceryl cocoate, and the water phase comprising solubilized 4-hydroxyacetophenone with niacinamide, wherein the weight ratio of niacinamide to 4-hydroxyacetophenone in the water phase is at least 3.0, and wherein one or more humectants may be present in the cosmetic composition, and:
the 4-hydroxyacetophenone is present in an amount from about 0.15% to 0.6%, by weight, based on the total weight of the cosmetic composition;
the total amount of the one or more humectants is 5.5% by weight or less, based on the total weight of the cosmetic composition;
the niacinamide is present in an amount from about 1% to about 2.2%, by weight, based on the total weight of the cosmetic composition and
the isohexadecane is present in an amount from about 4% to about 12% by weight, based on the total weight of the cosmetic composition,
wherein the cosmetic composition is free of essential oils other than fruit extracts, aloe vera extract, and seaweed extract.

10. The cosmetic composition of claim 9, wherein the cosmetic composition has been formed by the steps consisting essentially of providing an aqueous composition having the 4-hydroxyacetophenone and the niacinamide, and combining the aqueous composition with an oil composition having the at least one branched or linear, liquid alkane with carbon chain length of C11 to C20 comprising isohexadecane and the at least one alkylated glycerol ester surfactant comprising PEG-7 glyceryl cocoate.

11. The cosmetic composition of claim 9, wherein the niacinamide comprises niacinamide or its derivatives chosen from nicotinic acid, nicotinamide riboside, niacinamide ascorbate, salts thereof, or a combination thereof.

12. The cosmetic composition of claim 9, further comprising:
a) at least one polar emollient with molecular weight of 400 g/mol or less; and
b) at least one polymeric thickener for water-based system, wherein water is present in the cosmetic composition in an amount from about 70% to about 85% by weight of the cosmetic composition.

13. The cosmetic composition according to claim 12, wherein:
a) the at least one polar emollient with molecular weight of 400 g/mol or less comprises isopropyl myristate present in an amount from about 4% to about 12% by weight, based on the total weight of the cosmetic composition; and
b) the at least one polymeric thickener for water-based system comprises carbomer and acrylate/C10-30 alkyl acrylate crosspolymer.

14. The cosmetic composition according to claim 12, wherein:
a) each of the at least one branched or linear, liquid alkane with carbon chain length of C11 to C20 comprising isohexadecane is present from about 5% to about 10% by weight of the cosmetic composition;
b) each of the at least one polar emollient with molecular weight of 400 g/mol or less is present from about 5% to about 10% by weight of the cosmetic composition;
c) each of the at least one polymeric thickener for water-based system is present from about 0.01% to about 2% by weight of the cosmetic composition; and
d) the at least one alkylated glycerol ester surfactant comprising PEG-7 glyceryl cocoate is present up to 2.2% by weight of the cosmetic composition.

15. A makeup removal and cleansing article, comprising:
a. a water-insoluble substrate; and
b. impregnated in the water-insoluble substrate a cosmetic composition including a water phase, the water phase comprising solubilized 4-hydroxyacetophenone with niacinamide, wherein the weight ratio of niacinamide to 4-hydroxyacetophenone in the water phase is at least 3.0,
wherein:
the cosmetic composition is free of essential oils other than fruit extracts, aloe vera extract, and seaweed extract;
one or more humectants may be present in the cosmetic composition;
the total amount of the one or more humectants is 5.5% by weight or less, based on the total weight of the cosmetic composition; and
the niacinamide is present in an amount of about 1% to about 2.2%, based on the total weight of the cosmetic composition.

16. The makeup removal and cleansing article according to claim 15, wherein the article is a cosmetic removal wipe that comprises nonwoven fibers, the nonwoven fibers formed from natural, biodegradable and sustainably sourced fibers selected from (1) naturally originated fiber comprising one or more selected from pulp, viscose, lyocell, cellulose acetate, or cotton, (2) natural fiber comprising one or more selected from hemp, flax, seaweed, ramie, banana, or pineapple, (3) regenerated or recycled fiber comprising cotton, or (4) combinations thereof.

17. The makeup removal and cleansing article of claim 15, wherein in the cosmetic composition, the niacinamide comprises niacinamide or its derivative chosen from nicotinic acid, nicotinamide riboside, niacinamide ascorbate, salts thereof, or a combination thereof.

18. The makeup removal and cleansing article of claim 15, wherein the cosmetic composition further includes:
a) at least one branched or linear, liquid alkane with carbon chain length of C11 to C20, comprising isohexadecane present in an amount from about 4% to about 12% by weight, based on the total weight of the cosmetic composition;
b) at least one polar emollient with molecular weight of 400 g/mol or less comprising isopropyl myristate present in an amount from about 4% to about 12% by weight, based on the total weight of the cosmetic composition;
c) polymeric thickeners for water-based system comprising carbomer and acrylate/C10-30 alkyl acrylate crosspolymer; and
d) at least one surfactant comprising alkylated glycerol ester comprising PEG-7 glyceryl cocoate.

19. The makeup removal and cleansing article of claim 18, wherein in the cosmetic composition:
a) each of the at least one branched or linear, liquid alkane with carbon chain length of C11 to C20 comprising isohexadecane is present from about 5% to about 10% by weight of the cosmetic composition;
b) each of the at least one polar emollient with molecular weight of 400 g/mol or less comprising isopropyl myristate is present from about 5% to about 10% by weight of the cosmetic composition;
c) each of the polymeric thickeners for water-based system comprising carbomer and acrylate/C10-30 alkyl acrylate crosspolymer is present from about 0.01% to about 2% by weight of the cosmetic composition; and
d) the at least one surfactant comprising alkylated glycerol ester comprising PEG-7 glyceryl cocoate is present up to 2.2% by weight of the cosmetic composition.

* * * * *